(12) United States Patent
Rheinberger et al.

(10) Patent No.: US 8,067,482 B2
(45) Date of Patent: Nov. 29, 2011

(54) MATERIAL FOR PRODUCING PLASTIC MOLDED PARTS THAT CAN BE USED IN THE FIELD OF DENTISTRY

(75) Inventors: Volker Rheinberger, Vaduz (LI); Wolfgang Wachter, Eschen (LI); Gottfried Rohner, Altstätten (AT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 12/224,699

(22) PCT Filed: Mar. 2, 2007

(86) PCT No.: PCT/EP2007/051975
§ 371 (c)(1),
(2), (4) Date: Sep. 3, 2008

(87) PCT Pub. No.: WO2007/099158
PCT Pub. Date: Sep. 7, 2007

(65) Prior Publication Data
US 2009/0036612 A1    Feb. 5, 2009

(30) Foreign Application Priority Data
Mar. 4, 2006    (DE) .................... 10 2006 010 075

(51) Int. Cl.
*A61K 6/083* (2006.01)
(52) U.S. Cl. .......... 523/116; 523/120; 525/55; 525/902; 525/330.3; 525/244; 525/263; 433/218; 249/54
(58) Field of Classification Search .................. 523/116, 523/120; 525/55, 902, 330.3, 244, 263; 249/54; 433/218
See application file for complete search history.

(56) References Cited

U.S. PATENT DOCUMENTS

| | | | |
|---|---|---|---|
| 4,284,551 A | * | 8/1981 | Argentar ........................ 523/115 |
| 5,154,762 A | | 10/1992 | Mitra et al. |
| 2003/0069326 A1 | * | 4/2003 | Stangel et al. ................ 523/113 |

FOREIGN PATENT DOCUMENTS

| | | | |
|---|---|---|---|
| DE | 1 544 924 | | 7/1969 |
| DE | 198 41 342 | | 4/2000 |
| DE | 199 19 581 | | 11/2000 |
| DE | 101 37 968 | | 3/2003 |
| DE | 103 39 329 | | 3/2005 |
| DE | 103 55 992 | | 6/2005 |
| GB | 1442041 | * | 7/1976 |
| JP | 2005289961 A | * | 10/2005 |
| WO | WO 2004075862 A2 | * | 9/2004 |

OTHER PUBLICATIONS

The machine translation of JP 2005289961 A.*
Franco-Marques et al. Acta Biomaterialia, 2009, 5, 2953-2962.*
Partial English translation of JP 2005-289961 (2011).*
Database WPI Week 200577, Derwent Publications Ltd., London, GB, XP002465323 & JP 2005 289961 A (Matsukaze KK), Oct. 20, 2005.

* cited by examiner

*Primary Examiner* — Vasu Jagannathan
*Assistant Examiner* — Mark Kaucher
(74) *Attorney, Agent, or Firm* — Ann M. Knab

(57) ABSTRACT

A process for the preparation of plastic molded articles which can be used in the dental field, the process including the steps of: mixing A) at least one polymerizable component and B) at least one initiator in desensitized form to form a paste having a consistency does not demix during injection; injecting the paste into a cuvette; and polymerizing the mixture by applying heat.

7 Claims, No Drawings

MATERIAL FOR PRODUCING PLASTIC MOLDED PARTS THAT CAN BE USED IN THE FIELD OF DENTISTRY

The present invention relates to a material for the preparation of plastic molded articles which can be used in the dental field, in particular of dental prostheses, and to the use thereof.

Different materials and systems have been developed for many years by which dental prostheses can be prepared:

With regard to the temperatures to be used for carrying out the polymerization, a distinction is made between heat- and cold-curing systems. The boundary between the two systems is stipulated, according to ISO 1567:2000, at 65° C. An additional classification possibility is the method of the introduction of the polymerizable prosthetic substance into the prepared cuvette. In this connection, the "injection method" is particularly advantageous.

With regard to the starting materials, an additional division takes place, on the one hand, into the widespread powder/liquid systems and, on the other hand, into the single-component systems. In this connection, the powder/liquid system is totally dominant and comprises a monomer mixture (predominantly methyl (meth)acrylate) and a powder formed of a polymer which in most cases comprises a methyl (meth)acrylate homo- or copolymer and in addition can comprise additional fillers and coloring pigments.

The initiation system for the polymerization necessary in both cases is in principle always present in the components. In the self-curing systems, the initiator system is generally divided among the two components (powder and liquid) and is brought together by mixing the components. As soon as the mixture is prepared, only a certain handling time is left until curing takes place. As known in most chemical reactions, this time can be shortened by increasing the temperature. With heat-curing systems, the initiator is generally present in the polymer component and is distributed in the monomer matrix after mixing. The activation of these heat-curing systems and also of the single-component systems, which generally comprise peroxides, takes place predominantly by introduction of energy (heating, microwave energy, and the like).

In the past, different injection methods were then known which, however, still exhibit a number of disadvantages:

Thermoplastic injection methods process, similarly as in plastic injection molding, a normally noncrosslinkable thermoplastic which is injected into the cuvette above the softening point of the plastic. Due to the lack of crosslinking, the mechanical and chemical properties are in many cases unsatisfactory, so that these methods have never gained acceptance.

A widespread system of injection technology is the processing of cold-curing prosthetic plastics, the prosthetic methods of the firms Schütz Dental and Kulzer dominating. The disadvantage of these methods is that, in this connection, a self-activating initiation system is used which acts uniformly in the prosthetic substance and runs out fastest there where most heat arises. In this connection, it is not possible to compensate for the volume shrinkage arising in the polymerization, so that it is frequently necessary to fashion the prosthesis to the patient on fitting. However, the relatively short processing time of these methods is advantageous. In addition, the systems or improvements to the methods developed in recent years have simply resulted in a lessening of the problem without, however, actually being able to solve it.

In the processing of heat-curing prosthetic materials, the polymerization is triggered by increasing the temperature. The advantage in the processing by these materials is to be seen in the high monomer conversion and accordingly the low residual monomer content and a high chemical resistance of the prosthesis; however, the processing time is clearly longer and the fitting accuracy frequently poorer.

The most advanced method is the Ivocap method of Ivoclar Vivadent AG (likewise a heat-curing method), which can virtually completely compensate for the chemical polymerization shrinkage still occurring. This is guaranteed by a directed introduction of heat during the polymerization and a high injection pressure of still unpolymerized material. Only the heat shrinkage, which occurs when cooling polymerized molded articles to ambient temperature, can in this connection not be compensated for.

DE 940 493 describes a composition of two bead polymers based on (meth)acrylates. The object of this composition is advantageously to change the impasting and processing properties. This target is achieved by bringing the paste into a plastic kneadable condition as fast as possible, so that it can be introduced tack-free into a cuvette.

DE 24 08 640 proposes a solution to the shrinkage problem of cast plastics based on (meth)acrylate. In this connection, the considerable polymerization shrinkage of the monomers which occurs is to be reduced by reducing the proportion of the monomer phase in the mixture. This is achieved by adding solids to the monomer, these solids being partially dissolved in the monomer. Moreover, a balanced particle size distribution reduces the spacing of the individual fillers or polymer beads and thus makes possible optimized flow properties with the smallest possible monomer content. The initiators or coinitiators are present in the system in free form. They are accordingly extremely reactive and are not suitable for a thermally regulated polymerization.

The laid-open application DE 199 41 829 A1 describes a paste/paste system composed of two components which is distinguished by stable mixtures which cannot be changed further in the rheological properties. The polymers or fillers do not swell in the monomer phase. A disadvantage of such mixtures is that the bonding between filler and matrix is absent and the storage stability of the mixture with initiator is unsatisfactory.

DE 197 06 064 A1 describes a heat-curing dental single-component material which can be processed using the plugging/pressing technique. This material comprises no methyl (meth)acrylate but other known polyfunctional (meth)acrylate monomers which comprise PMMA bead polymers with a certain residual peroxide content as filler. These swell and give a processable paste. These substances are certainly not stable on storage since the bead polymers still exhibit a residual peroxide content from the process for the preparation thereof. In the example of this laid-open application, diluting is accordingly just carried out, so that the substances do not become too reactive and the storage stability is not further reduced.

DE 23 12 934 describes an injection method for two-component heat-cured polymers. The peroxide-comprising paste mixed immediately before polymerization is injected into a mold. In the water bath, the temperature is managed in regulated fashion in the interior of a cuvette via the geometry of the cuvette, where, through the heat, the polymerization reaction is started at relatively high temperatures. However, a self-polymerizable material cannot be processed with this system.

DE 24 03 211 describes an inorganic microfiller for dental composites. The material is preferably used for filling and dental substances. Prosthetic plastics are also mentioned in passing.

DE 64 049 322 describes a mixture of bead polymers composed of (meth)acrylate esters and the copolymers thereof. According to this document, the processing properties can be clearly improved by the use of blends of these bead polymers. However, a self-polymerization process is not known from this citation.

U.S. Pat. No. 5,154,762 describes a medical or dental cement composed of two components. These two components each comprise one component of the redox system, which can also each be microencapsulated. The storage stability of the two cement components is thereby supposed to be increased. At least one of the two microencapsulations is, in this connection, advantageously soluble in water.

DE 101 37 968 A1 describes dental filling materials based on two-component systems. In this connection, dental fillings are used in a reaction resin based on high boiling point methacrylates.

DE 15 44 924 A1 describes the use of peroxides in polymer beads. However, the peroxides are made accessible to the activating agents only by addition of monomers.

Furthermore, DE 103 55 992 A1, DE 198 41 342 A1 and DE 103 39 329 A1 describe the desensitization of initiators. However, this desensitization takes place using chemical methods. For example, phthalate esters are used for this. As a result, this leads to polymers of a quality which is not satisfactory for dental purposes.

It is now an object of the present invention to make available a system which is to combine the advantages of cold-cured polymerization (low polymerization temperatures, low thermal shrinkage, short processing times) with the hitherto outstanding properties of the injection method (good tooth adhesion, virtually complete compensation for polymerization shrinkage, high surface quality and good clinical durability).

This object is achieved through a material for the preparation of plastic molded articles which can be used in the dental field, comprising
A) at least one polymerizable component and
B) at least one initiator in desensitized form.

Virtually all monomers which are suitable for dental technology, in particular for the preparation of prostheses, are suitable as materials for the component A. The use of (meth) acrylates is particularly preferred and the use of methyl methacrylate is very particularly preferred.

An initiator system is preferably present in the component B and preferably comprises several components. These can be several initiators or also several activators. Mixtures of initiators and activators are likewise possible. In a particularly preferred embodiment, the initiator systems exist in the form of a combination of activator and initiator in spatially separated form. Particular preference is given in this connection to an initiator system comprising at least one activator and at least one initiator.

Within the meaning of this invention, the abovementioned spatial separation of individual components of the initiator system is to be understood as meaning that a separation of these components takes place through e.g., the encapsulation thereof in polymers and accordingly that no initiation of polymerization can yet be triggered. Furthermore, it is likewise possible for individual components of the initiator system also to be able to be present in the component A.

According to the invention, the initiator system comprises at least one initiator which triggers the polymerization reaction by radical formation. In addition, use may furthermore be made of an activator which accelerates this radical formation and accordingly the start of the polymerization reaction. If a redox system is used, even further components may be used. Depending on the type of polymerization (heat-cured, cold-cured or light-cured polymerization) which is being striven for, at least one of the components of the initiator system necessary for the polymerization is desensitized according to the invention. Consequently, either the activator or the initiator can thus be desensitized. The variant according to which both activator and initiator are desensitized is also preferred.

The term "desensitizing" is understood to mean, within the meaning of the invention, the lowering of the reactivity. That is, the initiator system allows only a slow down in the start of the polymerization. The result of this is that the components A and B can be stored for a longer period of time and, in the processing, a satisfactory handling time can be guaranteed and no premature polymerization is unleashed.

The desensitizing is, according to the invention, preferably achieved by an encapsulation of the initiator system components, preferably in a bead polymer.

By means of the desensitization described, it is possible to achieve a release of initiators and/or activators with selective delivery of heat at ambient temperature, that is in a system which is very inactive at temperatures of 12 to 28° C. Such could not be achieved with the hitherto conventional desensitizations of chemical systems. Such chemical desensitizations negatively affect, to be exact, the polymerization formulation and the energy balance. In particular, the low residual monomer contents desired for the dental field cannot be achieved with such chemical systems.

Accordingly, a physical encapsulation of the reactive components is striven for according to the invention. This can be achieved, for example, by a protective coating which is soluble in the monomer, permeable by delivery of heat, or a copolymerization in a microbead. Possible methods for microencapsulation are the in situ poly reaction, coacervation method, interface reaction, double emulsion method, phase separation method, and the like. The components can, after release by delivery of heat, react directly and thus guarantee high monomer conversions.

Preferred materials according to the invention for the preparation of plastic molded articles which can be used in the dental field, in particular dental prostheses, consist of a polymerizable component (A), which usually of a liquid mixture of polymerizable dental monomers and suitable solid fillers, and also at least one initiator in desensitized form (B) for the polymerization of the dental monomers. It is particularly preferable in this connection for the initiator or the components of the initiator system to be present or to be provided in desensitized form in the filler.

In a preferred alternative form of the invention, the desensitizing of the initiator system takes place in such a way that the components of the initiator system are encapsulated in a bead polymer so that swelling of the beads can only take place after mixing with the liquid monomer mixture. At the same time, a delayed release of the initiator components takes place as a result of the swelling.

A multitude of initiator systems are known from the state of the art which can likewise be used according to the invention, that is desensitized, for starting the polymerization reaction. However, use is preferably made of initiators for radical polymerization. The known initiators for cold and heat curing, light curing also being possible with an appropriately provided device, are suitable as initiators for radical polymerization.

Suitable initiators are described, for example, in the Encyclopedia of Polymer Science and Engineering, vol. 13, Wiley-Interscience Pub., New York, etc., 1988, p. 754 ff. Preferred initiators are peroxides, such as dibenzoyl peroxide, dilauroyl peroxide, tert-butyl peroctoate, tert-butyl perbenzoate or di(tert-butyl) peroxide, or azo compounds, such as azobisisobutyronitrile (AIBN) or azobis(4-cyanovaleric acid). Furthermore, perketals and benzopinacols are likewise suitable for heat curing. The initiation by peroxides or □-diketones is suitably accelerated in particular through combinations with activators, e.g. with aromatic amines. Redox systems can furthermore be used as initiator system, in particular combinations of dibenzoyl peroxide, dilauroyl peroxide or camphorquinone with amines, such as N,N-dimethyl-t-toluidine, N,N-dihydroxyethyl-p-toluidine, diethyl p-dimethylaminobenzoate or also other structurally related tertiary amines.

In addition, use is also made of redox systems which comprise, in addition to a peroxide, also ascorbic acid or the derivatives thereof, a barbiturate or a sulfinic acid as reducing agent.

Suitable photoinitiators for the UV or visible range are described by J. P. Fouassier and J. F. Rabek (editors), Radiation Curing in Polymer Science and Technology, vol. II, Elsevier Applied Science, London and New York, 1993, pages 155 to 237. Preferred photoinitiators are benzoin ethers, dialkyl benzil ketals, dialkoxyacetophenones, acylphosphine oxides, bisacylphosphine oxides and □-diketones, such as 10-phenanthrenequinone, diacetyl, furil, anisil, 4,4'-dichlorobenzil, 4,4'-dialkoxybenzil and camphorquinone.

The polymerization is, according to the invention, started at low temperature. Although the temperature climbs during polymerization (exothermicity of the reaction), the temperatures are clearly lower than in heat-cured polymerization. At the same time, two additional important process and product parameters are positively affected thereby. On the one hand, the thermally occasioned shrinkage of the prosthesis on cooling to ambient temperature is reduced and the fit of the dental prosthesis is improved and, on the other hand, the process times are reduced since, on the one hand, the temperature increase to the extent necessary for heat-cured polymers does not apply and, on the other hand, the cooling process is shorter due to the smaller difference in temperature between the highest point during the polymerization and the ambient or demolding temperature.

The great advantage of the powder/liquid systems with regard to tooth adhesion (in plastic teeth), which is caused by the swelling of the necks of the prosthetic teeth by the monomers of the liquid component, remains. In this connection, the monomer/the monomer mixture penetrates into the surface of the tooth necks and, with polymerization, a good bond is accordingly obtained between the tooth neck and the prosthetic material. If ceramic teeth are used, "crampons" (mechanical clasps) are used to achieve high mechanical retention.

An additional great advantage of the invention is that the technology known from the state of the art and available to the users (prosthetic dentistry laboratories) can be used and it is not necessary to acquire new items of equipment. Very particular preference is given to the use of the material according to the invention in the Ivocap method. With this, shrinkage compensation during the polymerization is likewise possible without any problems and the shrinkage caused by the polymerization is compensated for by forcing unpolymerized prosthetic substance into the cuvette. Since high pressures are used in this process, a high grade material (high homogeneity, no blisters in the prosthetic material) and a smooth surface and accordingly good clinical durability (reduced plaque deposition and proneness to discoloration) are achieved.

The release of the encapsulated initiator component can be accelerated by a selective rise in temperature. This encapsulation has the advantage that, on mixing the liquid component with the powder component, a satisfactorily long time is available for handling the polymerizable system and that, after the incorporation of the polymerizable substance in the cuvette, the release of the encapsulated initiator component can be accelerated by selective increase in temperature (controlled in time and in place) and accordingly the processing time can be brought into line with the size of the plastic molded article. A reservoir with unpolymerized prosthetic material outside the cuvette is in this connection naturally not heated, so that material from this reservoir can be forced into the cuvette and accordingly the polymerization shrinkage of the plastic in the cuvette can be compensated for.

The heating of the material in the cuvette preferably takes place in such a way that the temperature increase is carried out in the form of a "temperature front" which begins at the cuvette opposite the reservoir with the unpolymerized material and accordingly the polymerization starts at the "most distant" place inside the cuvette. The release of initiator is further accelerated by the exothermicity of the polymerization reaction and the heating in the adjoining regions inside the cuvette goes on until, finally, initiator is completely released and the polymerization completely takes place.

Accordingly, the polymerization can according to the invention be controlled by selective incorporation of heat. The corresponding temperatures lie in ranges from 20° C. to 90° C., preferably from 30° C. to 50° C. That is, the polymerization is started and controlled via the controlled delivery of heat. On using the materials according to the invention, additional energy is delivered in the further course of the preparation and processing. Through this, a temperature gradient is produced, it being possible to control reactions by adjusting this gradient.

The temperature gradient in the processing of the materials according to the invention starts from a starting temperature of 2° C. to 35° C., preferably of 12° C. to 28° C. The temperature can be increased in stages subsequently thereto. In this connection, the temperatures of the individual stages lie at temperatures of 20° C. to 90° C., preferably of 35° C. to 45° C. It is possible, with the materials according to the invention, to compensate, by forcing in material, for the polymerization shrinkage produced. The container used in the injection method retains in this connection its original temperature and provides the material forced in.

The materials according to the invention are preferably used in the dental field; the use for dental prostheses is particularly advantageous. The material according to the invention can particularly advantageously be used in combination with the injection method described at the start.

The use of the material according to the invention in such an injection method is described below using an example:

Preparation of the Mixture

The polymer powder is added to the monomer in the mixing ratio given above and thoroughly blended together. At the same time, the pigments are completely dispersed in the system. The mixture obtained is then poured into a disposable capsule sealed at the beginning. The consistency of the unpolymerized substances should ideally, after the mixing of the two components, be thin enough to flow, so that small air bubbles stirred in can rise and if possible no small air inclusions are present in the capsule reservoir.

At the same time, the material further thickens, so that an injectable paste is formed with increasing "maturity" of the mixture. Injectable means that the consistency of the paste has increased so much that, during injection, demixing can no longer take place and, as it flows in, the stream has the most laminar structure possible. This consistency is achieved after approximately 5 to 10 minutes after the start of mixing.

The chemical polymerization shrinkage which occurs is now virtually completely compensated for by material which flows in subsequently, analogously to the well-known Ivocap method. The heat shrinkage is clearly reduced in comparison with the conventional heat-cured polymers, such as the Ivocap method.

Cooling takes place either directly in the injector, e.g. via air cooling, or, however, the cuvette is removed from the injector and is cooled at ambient temperature in the air or in cold flowing water. It is then removed from the mold as usual. It is important in this connection for the temperature in the cuvette to have fallen so much that dimensional stability exists with regard to mechanical stress.

EXAMPLES FOR SELF-CURING SYSTEMS

Formulation 1 Polymer

55% Degacryl M 527 (polymeric methacrylate with mean particle size approximately 50 μm)
30% Degacryl MW 332 (polymeric methacrylate with mean particle size approximately 45 μm)
7.5% Encapsulated initiator/polymer with 2.5% 1-benzyl-5-phenylbarbituric acid (mean particle size approximately 65 μm)
  i.e., the initiator system for the self-curing consists of barbituric acid derivative which, for the purposes of desensitization, is enclosed in a polymer. The polymer is a PMMA bead polymer.
7.5% Pigments, modifiers, stabilizers, support polymers for pigments, and the like.

Mixing and homogenizing is carried out in the powder mixing process (e.g. drum mixer).

Mixing of this mixture is carried out by hand in the ratio 10 g of powder/5 g of monomer (ProBase Cold from Ivoclar Vivadent AG, Liechtenstein). This mixture has an exothermic reaction at 23° C. of >45 minutes but nevertheless the initiator content is high enough to achieve complete curing of the mixture.

Formulation 2

60% Degacryl M527 (Rohm GmbH, polymeric methacrylate with mean particle size approximately 50 μm)
30Degacryl MW332 (Rohm GmbH, polymeric methacrylate with mean particle size approximately 45 μm)
2.5% Encapsulated initiator/polymer with 0.5% BPO (mean particle size approximately 65 μm)
7.5% Pigments, modifiers, stabilizers, support polymers for pigments, and the like.

Mixing and homogenizing are carried out in the powder mixing process (e.g. drum mixer). The initiator/polymer is a bead polymer and consists of a copolymer of MMA (85%) and ethylene glycol dimethacrylate (15%).

Mixing of this mixture is carried out by hand in the ratio 10 g of powder/5 g of monomer (Triplex Cold from Ivoclar Vivadent AG, Liechtenstein). This mixture has an exothermic reaction at 23° C. of >45 minutes but nevertheless the initiator content is high enough to achieve complete curing of the mixture.

EXAMPLES FOR HEAT-CURING SYSTEMS

Formulation 3

80% Degacryl M527 (Rohm GmbH, polymeric methacrylate with mean particle size approximately 50 μm)
20% Encapsulated initiator/polymer with 0.5% AIBN (mean particle size approximately 45 μm)
  i.e. the initiator system for the heat curing consists of the thermal initiator AIBN (N,N-azobisisobutyronitrile) which, for the purposes of desensitization, is enclosed in a polymer. The initiator/copolymer (bead polymer) consists of urethane dimethacrylate (70%), MMA (25%) and ethylene glycol dimethacrylate (5%).

Mixing and homogenizing are carried out in the powder mixing process (e.g. drum mixer).

Mixing of this mixture is carried out by hand in the ratio of 10 g of powder/5 g of monomer (ProBase Hot, Ivoclar Vivadent AG, Liechtenstein). These mixtures are, thanks to the desensitizing of the initiator, stable on storage even in the mixed condition at 23° C. for several months. Nevertheless, the initiator content is high enough to achieve complete curing of the mixture in a heat curing (>65° C.).

Preparation Method for Prostheses

Formulations 1 and 2 can be processed to give prosthetic substances which comply with the standard ISO 1567:2000 for cold-cured polymers and also for heat-cured polymers.

Furthermore, formulations 1 and 2 can be used as conventional cold-cured polymers with a greatly extended processing time in the casting procedure and the plugging procedure. Furthermore, it can be used as repair material.

Formulation 3 can be used in a heat-curing polymerization process, in the "plugging method".

The invention claimed is:

1. A process for the preparation of dental prostheses, wherein an initiator system is present in the form of a combination of an activator and an initiator in spatially separated form, comprising the steps of:
  mixing A) at least one polymerizable component in liquid form and B) a powder component containing at least one initiator in desensitized form to form a paste having a consistency that does not demix during injection;
  injecting the paste into a cuvette from a reservoir; and
  polymerizing the mixture by applying heat, wherein the activator is in the polymerizable component, and wherein the desensitization of the initiator in the powder component is provided by encapsulation in a bead polymer;
  wherein the heating of the mixture in the cuvette takes place in such a way that the temperature increase is carried out in the form of a temperature front which begins at the cuvette opposite the reservoir containing the unpolymerized mixture starting the polymerization at the most distant place inside the cuvette; and
  wherein the polymerization is controlled by selective incorporation of heat in the range of from 30° to 50° C.

2. The process as claimed in claim 1, wherein mixing is carried out for 5 to 10 minutes.

3. The process as claimed in claim 1, wherein the polymerizable component A is a (meth)acrylate.

4. The process as claimed in claim 1, wherein the bead polymer is swellable in the component A.

5. The process as claimed in claim 1, wherein the bead polymer comprises (meth)acrylate.

6. The process as claimed in claim 1, including utilizing initiators as initiators for cold-or heat-curing.

7. The process as claimed in claim 1, wherein the initiator is a cold-curing initiator.

* * * * *